US00PP33215P2

(12) United States Plant Patent
Koot

(10) Patent No.: US PP33,215 P2
(45) Date of Patent: Jun. 29, 2021

(54) ***VERBENA* PLANT NAMED 'DOVEREMSUCORE'**

(50) Latin Name: ***Verbena* X *hybrida***
Varietal Denomination: Doveremsucore

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,889

(22) Filed: Aug. 4, 2020

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — C. Anne Whealy

(57) ABSTRACT

A new and distinct cultivar of *Verbena* plant named 'Doveremsucore', characterized by its compact, mounding to semi-trailing plant habit; moderately vigorous growth habit; freely branching habit; early and freely flowering habit; large vivid red-colored flowers; and good garden performance.

1 Drawing Sheet

Botanical designation: *Verbena* X *hybrida*.
Cultivar denomination: 'DOVEREMSUCORE'.

STATEMENT REGARDING PRIOR DISCLOSURES BY THE INVENTOR AND APPLICANT

The Inventor and Applicant assert that no sales, publications or advertisements relating to sales, offers for sale or public distribution occurred more than one year prior to the effective filing date of this application. Any information about the claimed plant would have been obtained from a direct or indirect disclosure from the Inventor and/or the Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Verbena* plant, botanically known as *Verbena* X *hybrida* and hereinafter referred to by the name 'Doveremsucore'.

The new *Verbena* plant is a product of a planned breeding program conducted by the Inventor in Rheinberg, Germany. The objective of the breeding program is to create new compact and early-flowering *Verbena* plants with numerous large and attractive flowers.

The new *Verbena* plant originated from a cross-pollination made by the Inventor in July, 2017 in Rheinberg, Germany of a proprietary selection of *Verbena* X *hybrida* identified as code number VV16-006794-001, not patented, as the female, or seed, parent with a proprietary selection of *Verbena* X *hybrida* identified as code number VV16-003808-001, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2019.

Asexual reproduction of the new *Verbena* plant by terminal vegetative cuttings in a controlled greenhouse environment in Rheinberg, Germany since June, 2019 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doveremsucore'. These characteristics in combination distinguish 'Doveremsucore' as a new and distinct *Verbena* plant:

1. Compact, mounding to semi-trailing plant habit.
2. Moderately vigorous growth habit.
3. Freely branching habit.
4. Early and freely flowering habit.
5. Large vivid red-colored flowers.
6. Good garden performance.

Plants of the new *Verbena* differ primarily from plants of the female parent selection in flower color as plants of the new *Verbena* have darker and more intense red-colored flowers than plants of the female parent selection.

Plants of the new *Verbena* differ primarily from plants of the male parent selection in plant habit as plants of the new *Verbena* are more compact than and not as vigorous as plants of the male parent selection.

Plants of the new *Verbena* can be compared to plants of the *Verbena hybrida* 'Sunmarired' disclosed in U.S. Plant Pat. No. 18,615. In side-by-side comparisons, plants of the new *Verbena* differ primarily from plants of 'Sunmarired' in the following characteristics:

1. Plants of the new *Verbena* are more compact than and not as vigorous as plants of 'Sunmarired'.

2. Plants of the new *Verbena* are somewhat more freely branching than plants of 'Sunmarired'.
3. Plants of the new *Verbena* have larger and lighter green-colored leaves than plants of 'Sunmarired'.
4. Plants of the new *Verbena* have larger flower inflorescences with larger flowers than plants of 'Sunmarired'.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant. The photograph is a side perspective view of a typical flower plant of 'Doveremsucore' grown in a container.

DETAILED BOTANICAL DESCRIPTION

The aforementioned photograph and following observations, measurements and values describe plants grown in 22-cm containers during the spring and early summer in a glass-covered greenhouse in Rheinberg, Germany and under cultural practices typical of commercial *Verbena* production. During the production of the plants, day and night temperatures averaged 18° C. and light levels averaged 4,500 lux. Plants were pinched one time three weeks after planting and were twelve weeks old when the photograph and description were taken. In the description, color references are made to The Royal Horticultural Society Colour Chart, Fifth Edition, 2007, except where general terms of ordinary dictionary significance are used.

Botanical classification: *Verbena* X *hybrida* 'Doveremsucore'.

Parentage:

*Female, or seed, parent.*—Proprietary selection of *Verbena* X *hybrida* identified as code number VV16-006794-001, not patented.

*Male, or pollen, parent.*—Proprietary selection of *Verbena* X *hybrida* identified as code number VV16-003808-001, not patented.

Propagation:

*Type.*—Terminal vegetative cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; close to 158A in color, actual color of the roots is dependent on substrate composition, water quality, fertilizers, substrate temperature and age of roots.

*Rooting habit.*—Freely branching; medium density.

Plant description:

*Plant habit.*—Compact, mounding to semi-trailing plant habit; freely branching habit with about seven primary lateral branches each with about eight secondary lateral branches; pinching enhances lateral branch development; dense and bushy plant habit; moderately vigorous growth habit; moderate growth rate.

*Plant height, soil level to top of foliar plane.*—About 26 cm.

*Plant height, soil level to top of floral plane.*—About 26 cm.

*Plant diameter.*—About 65 cm.

Lateral branch description:

*Length.*—About 20 cm.

*Diameter.*—About 4 mm.

*Internode length.*—About 2.8 cm.

*Strength.*—Strong.

*Texture and luster.*—Pubescent; semi-glossy.

*Color, developing and developed.*—Close to 144A.

Leaf description:

*Arrangement.*—Opposite, simple.

*Length.*—About 3.9 cm.

*Width.*—About 2.4 cm.

*Shape.*—Lanceolate.

*Apex.*—Acute.

*Base.*—Attenuate.

*Margin.*—Lobed; sinuses medium in depth and divergent.

*Texture and luster, upper surface.*—Pubescent, coarse; semi-glossy.

*Texture and luster, lower surface.*—Pubescent, coarse; matte.

*Venation pattern.*—Pinnate.

*Color.*—Developing leaves, upper surface: Close to 137A. Developing leaves, lower surface: Close to 137D. Fully expanded leaves, upper surface: Close to 137B; venation, close to 137B. Fully expanded leaves, lower surface: Close to 137D; venation, close to 137D.

*Petioles.*—Length: About 4.1 mm. Diameter: About 2 mm. Strength: Moderately strong. Texture and luster, upper and lower surfaces: Smooth, glabrous; matte. Color, upper and lower surfaces: Close to 145A.

Flower description:

*Flower arrangement and habit.*—Salverform flowers arranged in hemispherical terminal umbels; umbels dense and mounding; numerous umbels per plant; flowers face upward or outwardly depending on position in the umbel; freely flowering habit with about 16 flowers per inflorescence and about 190 flowers and flower buds per plant at one time.

*Fragrance.*—None detected.

*Natural flowering season.*—Plants flower continuously from the spring through the fall in Germany; plants begin flowering about eight weeks after planting.

*Flower longevity.*—Individual flowers last about one week on the plant; flowers persistent.

*Inflorescence height.*—About 2.9 cm.

*Inflorescence diameter.*—About 6.2 cm.

*Flower buds.*—Length: About 1.5 cm. Diameter: About 2.8 mm. Shape: Oval to tubular. Texture and luster: Rippled; matte. Color: Close to 53B.

*Flowers.*—Appearance: Salverform, five-parted fused corolla. Diameter: About 1.9 cm. Depth: About 2.7 cm. Throat diameter: About 1.7 mm. Tube length: About 2 cm. Tube diameter: About 1.6 mm.

*Corolla.*—Arrangement: Single whorl of five fused petals. Petal lobe length: About 1.2 cm. Petal lobe width: About 1 cm. Petal lobe shape: Obovate. Petal lobe apex: Emarginate. Petal margin: Entire. Petal texture and luster, upper and lower surfaces: Smooth, glabrous; matte. Throat texture and luster: Smooth, glabrous; matte. Tube texture and luster: Smooth, glabrous; matte. Color: Petal lobe, when opening, upper surface: Close to 46B. Petal lobe, when opening, lower surface: Close to 50A. Petal lobe, fully opened, upper surface: Close to 45B; venation, close to 45B; color does not change with development. Petal lobe, fully opened, lower surface: Close to 51A; venation, close to 51A, color does not change with development. Throat: Close to 145C; venation, close to 145C. Tube: Close to 145D; venation, close to 145C.

*Calyx.*—Arrangement: Star-shaped calyx with five fused sepals. Length: About 1.1 cm. Diameter: About 2.5 mm. Sepal length: About 1.1 cm. Sepal width: About 0.8 mm. Sepal shape: Ligulate. Sepal apex: Acute. Sepal margin: Entire. Sepal texture and luster, upper surface: Pubescent, coarse; semi-glossy. Sepal texture and luster, lower surface: Pubescent, coarse; matte. Sepal color, when developing, upper and lower surfaces: Close to 144A and 144C. Sepal color, fully developed, upper and lower surfaces: Close to 146B and 145C.

*Peduncles.*—Length: About 4 cm. Diameter: About 2 mm. Strength: Strong. Aspect: Mostly upright. Texture and luster: Pubescent; semi-glossy. Color: Close to 146B.

*Pedicels.*—Length: About 0.5 mm. Diameter: About 0.5 mm. Strength: Strong. Aspect: Mostly upright. Texture and luster: Smooth, glabrous; semi-glossy. Color: Close to 144A.

*Reproductive organs.*—Stamens: Quantity and arrangement: About four per flower, adnate to corolla tube. Filament length: About 1 mm. Filament color: Close to 155C. Anther length: About 0.8 mm. Anther shape: Oval. Anther color: Close to 144B. Pollen amount: Moderate. Pollen color: Close to 2C. Pistils: Quantity: One per flower. Pistil length: About 1.8 cm. Style length: About 1.7 cm. Style color: Close to 144D. Stigma diameter: About 0.8 mm. Stigma shape: Bi-parted; fimbriate. Stigma color: Close to 144A. Ovary color: Close to 144C. Fruits: Quantity produced per plant: About 190 during the flowering season. Length: About 7 mm. Diameter: About 1.8 mm. Texture: Rough. Color: Close to 199D. Seeds: Quantity per flower: About four. Length: About 4 mm. Diameter: About 1.2 mm. Texture: Smooth, glabrous. Color: Close to 199A.

Garden performance: Plants of the new *Verbena* have been observed to have good garden performance, to tolerate temperatures ranging from 5° C. to 40° C. and to be suitable for USDA Hardiness Zone 11.

Pathogen & pest resistance: To date, plants of the new *Verbena* have not been observed to be resistant to pathogens and pests common to *Verbena* plants.

It is claimed:

1. A new and distinct *Verbena* plant named 'Doveremsucore' as illustrated and described.

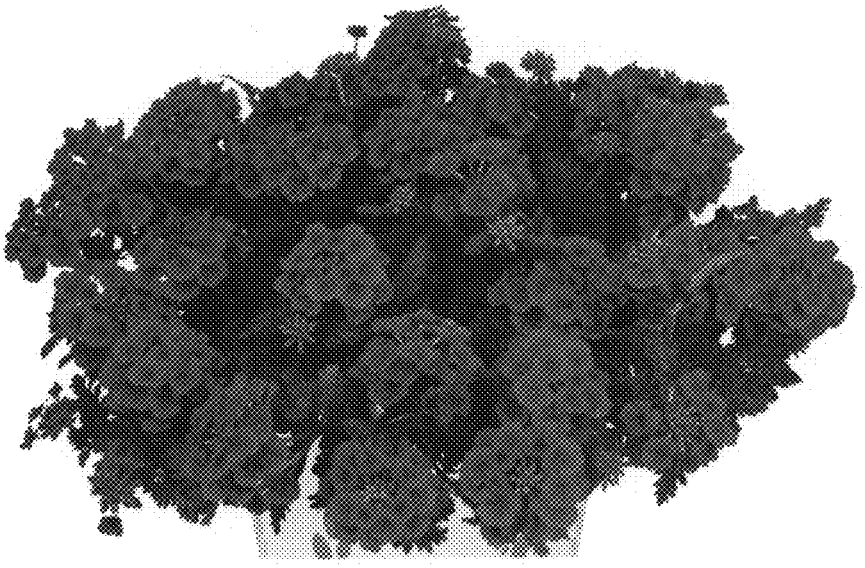

* * * * *